(12) United States Patent
Schroeter

(10) Patent No.: US 10,105,461 B2
(45) Date of Patent: *Oct. 23, 2018

(54) DEVICE FOR FACILITATING A CHEMICAL REACTION

(71) Applicant: Todd Schroeter, Medina, OH (US)

(72) Inventor: Todd Schroeter, Medina, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/703,538

(22) Filed: May 4, 2015

(65) Prior Publication Data

US 2015/0231292 A1 Aug. 20, 2015

Related U.S. Application Data

(63) Continuation of application No. 13/805,184, filed as application No. PCT/US2011/041011 on Jun. 18, 2011, now Pat. No. 9,050,570.

(Continued)

(51) Int. Cl.
*A61L 2/20* (2006.01)
*B65B 29/10* (2006.01)
(Continued)

(52) U.S. Cl.
CPC ............... *A61L 2/20* (2013.01); *B01J 8/009* (2013.01); *B65B 3/00* (2013.01); *B65B 7/16* (2013.01);
(Continued)

(58) Field of Classification Search
CPC ...... B01J 7/02; A61L 2/18; A61L 2/20; C01B 11/024
(Continued)

(56) References Cited

U.S. PATENT DOCUMENTS 4,060,175 A 11/1977 Rysgaard, Sr.
5,126,070 A 6/1992 Leifheit et al.
(Continued)

FOREIGN PATENT DOCUMENTS

WO 03/051406 A1 6/2003
WO 2006022676 A2 6/2006
WO 2006068743 A2 6/2006

OTHER PUBLICATIONS

International Search Report and Written Opinion from corresponding PCT/US2011/041011 dated Apr. 6, 2012.
(Continued)

*Primary Examiner* — Lessanework Seifu
(74) *Attorney, Agent, or Firm* — Lando & Anastasi, LLP

(57) ABSTRACT

A device for facilitating a chemical reaction that includes an upper member, a lower member, and a dissolvable member disposed between them such that upper and lower chambers are formed having substantially equal volumes. The upper chamber receives a dry sodium chlorite and the lower chamber receives a dry acid mixture. The upper and lower members are joined, thereby sealing the upper and lower chambers and enabling the joined upper and lower members to be disposed in water such that said lower member engages the water first. The joined upper and lower members swell with absorbed water to engage the dry sodium chlorite and the dry acid mixture to form slurries to dissolve the dissolvable member to allow the slurries to react to generate chlorine dioxide gas that passes through the upper and lower members and into a space to be disinfected and/or deodorized.

13 Claims, 5 Drawing Sheets

Related U.S. Application Data

(60) Provisional application No. 61/397,931, filed on Jun. 18, 2010.

(51) Int. Cl.
*B01J 8/00* (2006.01)
*B65B 7/16* (2006.01)
*B65B 3/00* (2006.01)

(52) U.S. Cl.
CPC ..... *B65B 29/10* (2013.01); *B01J 2208/00814* (2013.01)

(58) Field of Classification Search
USPC .................................................. 422/238, 239
See application file for complete search history.

(56) References Cited

U.S. PATENT DOCUMENTS

| | | |
|---|---|---|
| 6,764,661 B1 | 7/2004 | Girard |
| 7,160,484 B2 | 1/2007 | Thangaraj et al. |
| 7,534,398 B2 | 5/2009 | Dee et al. |
| 2004/0022676 A1 | 2/2004 | Hamilton et al. |
| 2006/0039840 A1 | 2/2006 | Chia et al. |

OTHER PUBLICATIONS

Office Action of the Canadian Intellectual Property Office from corresponding CA Application Serial No. 2,803,133 dated Jun. 22, 2017.

DEVICE FOR FACILITATING A CHEMICAL REACTION

CROSS-REFERENCE TO RELATED APPLICATIONS

This application is a continuation of U.S. patent application Ser. No. 13/805,184, filed Dec. 18, 2012, which is a 371 U.S. National Stage of International Application No. PCT/US2011/041011, filed on Jun. 18, 2011, which claims priority to and the benefit of U.S. Provisional Application No. 61/397,931, filed on Jun. 18, 2010. The contents of the above applications are incorporated herein by reference in their entirety.

BACKGROUND OF THE INVENTION

Field of the Invention

This invention relates to a device for facilitating a chemical reaction, and more particularly, to a device and method for facilitating the generation of chlorine dioxide gas for release into air or water.

Background of the Prior Art

Chlorine dioxide gas is a well known disinfectant and deodorizing agent that can be generated as a gas for release into air or water. Chlorine dioxide gas is soluble and does not hydrolyze in water, but remains as a true gas in water. It is common to use sodium chlorite and an acid, both in dry form, combined with an aqueous solution to generate chlorine dioxide. The problem with conventional non-electrically powered chlorine dioxide gas generators using dry sodium chlorite and an acid has been the membrane shells forming the cavities that receive the dry sodium chlorite and acid. More specifically, prior art membranes are substantially impervious to liquid and have been designed to protect the dry internal components from moisture to promote shipping and handling of the device without activation.

Unfortunately, the water protective membranes have increased the reaction time required for completing the chlorine dioxide gas generation from the combining of the sodium chlorite and acid after exposure to water. The water protective membranes increase the reaction time because a wick member must be used to transport water into the membrane shell, thereby increasing the time required to dispose water inside the shell due to the relatively small cross sectional area of the wick penetrating the shell. Further, although the membranes are semi-permeable to chlorine dioxide gas, the flow of chlorine dioxide gas is restricted through the membranes during gas generation thereby restricting "breathability" of the shell.

Another problem with prior art chlorine dioxide gas generators is that only one cavity is provided to receive a mixture of sodium chlorite and acid. The mixing of the reactants results in inconsistencies and varying contact ratios between the sodium chlorite and acid resulting in varying quantities of chlorine dioxide gas being generated when water engages the reactants.

The mixed internal components form different surface areas of sodium chlorite that engage acid relative to the wick member. When water initially engages the internal components adjacent to the wick member, then travels to internal components further from the wick member, varying amounts sodium chlorite react with varying amounts of acid, thereby providing slower and/or incomplete reactions between the sodium chlorite and acid, resulting in wasted residual portions of each internal component which must be discarded and which did not generate any chlorine dioxide.

U.S. Pat. No. 5,126,070, issued to Leifheit et al. on Jun. 30, 1992, discloses a rupturable or frangible pouch and an absorbent carrier for reacting a chlorite and an acid to form chlorine dioxide gas. The speed of chlorine dioxide gas formation is dependent upon the manual force applied to the package to combine the internal components.

U.S. Pat. No. 6,764,661, issued to Girard on Jul. 20, 2004, discloses wick means extending into and connected to a membrane shell defining a compartment. A wick member extends outside of the compartment. The wick member absorbs water outside of the compartment and transports the water into the compartment to expose the components therein to water to produce chlorine dioxide gas.

In general, the prior art devices and methods do not provide sufficient surface area to fully utilize all of the supplied chemical and to cause a complete reaction between sodium chlorite and acid such that there is no "unused" portions of either component, which results in a less than maximum formation of chlorine dioxide gas. More specifically, the prior art devices resort to manual force or added components (wick means) to urge the engagement of sodium chlorite, acid and water instead of using the relatively large surface area of the packet containing the components to ultimately expose the components to an aqueous solution. Further, the prior art devices do not use a material for constructing the packets or shells that are capable of allowing a relatively large quantity of water to flow relatively quickly through the shell to engage the internal components, and that allows generated chlorine dioxide gas to escape relatively fast through shell and into the surrounding air and/or water. Also, although the material of construction should allow water through the shell, the material must resist atmospheric moisture to prevent premature activation of the internal components. Another problem with the prior art is that the packets are not rigid and therefore change shape after disposing dry reactants into chambers, resulting in less than full chambers, non-uniform distribution of the dry chemicals in the packet, and dry chemicals that vary in configuration when the orientation of the packet is changed, thereby reducing chlorine dioxide generation and allowing residual unused chemicals.

SUMMARY OF THE INVENTION

It is an object of the present invention to overcome many of the disadvantages associated with prior art devices for facilitating a chemical reaction.

A principal object of the present invention is to provide a device for facilitating a chemical reaction between a liquid catalyst and one or more dry reactants within device to produce a gas and/or liquid that is ultimately released into air and/or liquid. A feature of the device is the generation of a gas by acid activation. Another feature of the device is enclosure or packet fabrication material that encases the dry reactants and that allows the liquid catalyst to penetrate the packet relatively quickly and engage the dry reactants therein. An advantage of the device is that the one or more dry reactants are totally enclosed in a packet, and in the case of two or more reactants being present, the two or more reactants are separated and totally enclosed within the packet in cooperatively configured chambers, each chamber being completely filled with a respective dry reactant, thereby allowing the totally enclosed one or more dry reactants to be manually disposed in the liquid catalyst. Another advantage of the device is that the generation of a gas by acid activation occurs without the use of an external force to rupture the packet. Yet another advantage of the device is that the generation of a gas by acid activation occurs without the addition of a wick member to absorb and transport the liquid catalyst into the packet. Still another advantage of the device is that a material for fabricating the packet allows a relatively large quantity of water to flow relatively quickly into the packet to engage the internal components, the material of fabrication also allowing generated chlorine dioxide gas to escape the packet relatively fast and into the surrounding air and/or water. Another advantage of the device is that the material of fabrication allows water through the shell, yet the material resists atmospheric moisture to prevent premature activation of the internal components. Another advantage of the device is that the packets are rigid and therefore do not change shape after disposing dry reactants into the chambers, resulting in continuously full chambers of the dry chemicals that maintain a constant configuration within the packet, which causes consistent chorine dioxide generation irrespective of packet orientation.

Another object of the present invention is to provide a device that facilitates acid activation to produce a gas or liquid. A feature of the device is a packet having an upper member, a lower member and a dissolvable member disposed between and enclosed by the upper and lower members such that upper and lower chambers are formed having substantially equal volumes. Yet another feature of the device is a holder member for receiving a predetermined quantity of liquid catalyst and the packet. An advantage of the device is that the packet is ultimately disposed in the liquid catalyst such that the lower member engages the liquid catalyst first, thereby allowing a bottom compressed sponge cloth to engage the water and expand and be reconfigured such that the edges are contorted upward creating a cupping action or concave up configuration, resulting in a substantially wet acid engaging one side of the dissolvable member and a substantially dry sodium chlorite engaging the opposite side of the dissolvable member. The now expanded bottom sponge cloth cooperates with the upper compressed sponge such that when the upper compressed sponge absorbs sufficient now acidified water to fully expand, the bottom sponge cloth reverts to a planar configuration to dispose the reactants of the upper and lower chambers closer together. Another advantage of the device is that the lower and upper members cooperate to allow a predetermined quantity of liquid catalyst to penetrate the lower member and engage the acid reactant in the lower chamber followed by the now acidic liquid catalyst in the lower member being absorbed by the upper member through periphery contact at the sewn edges, then engaging the substantially dry reactant in the upper chamber to begin the conversion of sodium chlorite to chlorine dioxide and to ultimately form slurries that completely dissolve the dissolvable member to allow the slurries to engage in the continuous reaction of chlorine dioxide by the acid slurry and sodium chlorite slurry until all chemicals have been exhausted.

Yet another object of the present invention is to provide a device that facilitates generation of chlorine dioxide gas for release into water. A feature of the device is a packet having an upper and lower members fabricated from a compressed sponge cloth with a dissolvable member disposed between and enclosed by the upper and lower members such that upper and lower chambers are formed having substantially equal volumes. Another feature of the device is a packet having an upper chamber substantially filled with sodium chlorite, and having a lower chamber substantially filled with an acid mixture. An advantage of the device is that compressed sponge cloth material for fabricating the packet allows a relatively large quantity of water to seep relatively quickly into the packet to engaging and completely filling the internal components, the material of fabrication also allowing generated chlorine dioxide gas to escape the packet after an incubation period into the surrounding water. An advantage of the device is that water absorbed by the compressed sponge cloth has sufficient quantity to transform the sodium chlorite and the dry acid mixture into slurries quickly to dissolve the dissolvable member to allow the slurries to engage and ultimately react to generate chlorine dioxide gas that ultimately passes through the upper and lower members in relatively large quantities into a surrounding liquid to be disinfected and/or deodorized.

Still another object of the present invention is to provide a device that includes a packet fabricated from material that allows a relatively large quantity of water to flow relatively quickly into the packet to engage the internal components, the material of fabrication also allowing generated chlorine dioxide gas to escape the packet through the upper member relatively fast and into the surrounding air, the material of fabrication ultimately absorbing all water in a holder member that the packet is disposed in. A feature of the device is an upper member fabricated from compressed cellulose sponge and a lower member fabricated from cellulose cloth material. The compressed cellulose cloth and compressed cellulose sponge have closed pores and fiber structure when compressed, the pores ultimately opening when the lower and upper members absorb water, thereby allowing generated chlorine dioxide gas to escape the joined upper and lower members. An advantage of the device is that the compressed cellulose cloth material and compressed sponge material promote retention of sodium chlorite and acid slurries in corresponding upper and lower chambers until the reaction for generating chlorine dioxide gas is complete and without leaving any residue of sodium chlorite or acid. Another advantage of the device is that the joined upper and lower members of compressed sponge material and compressed cellulose cloth material retains the absorbed water during the entire reaction time for forming chlorine dioxide gas, and continues to retain the water after the reaction has completed, thereby allowing the packet and absorbed water to be disposed of without any appreciable water residue in the holder member.

Another object of the present invention is to provide a device that includes a dissolvable member having a configuration that promotes a relatively faster and more complete chlorine dioxide gas generation and conversion rates. A feature of the device is a dissolvable member having an undulating or "wave" configuration that provides a trough or recess that receives sodium chlorite therein to maintain the sodium chlorite in the recess irrespective of the orientation of the packet. Another feature of the device is that the wall of the recess of the dissolvable member provides more surface area than a planar dissolvable member, thereby increasing cooperating quantities of sodium chlorite and acid mixture disposed adjacently on opposite sides of the dissolvable member. An advantage of the device is that when the dissolvable member is dissolved by acid and sodium chlorite slurries, the increased quantities of sodium chlorite and acid slurries that immediately mix together ultimately generates chlorine dioxide gas at a faster rate than the gas rate generated by relatively smaller slurry quantities that mix after a planar dissolvable member is dissolved. Another advantage of the device is that chlorine dioxide gas generation rate for a packet can be increased or decreased by correspondingly increasing or decreasing the surface area of the trough or recess, and the surface area of the recess is varied by correspondingly changing the configuration and/or dimensions of the dissolvable member.

Briefly, the invention provides a device for facilitating a chemical reaction comprising an upper member having a predetermined configuration, said upper member being rigid and not reconfigurable thereby maintaining the configuration of dry sodium chlorite disposed into an upper chamber, resulting in a continuously full upper chamber of said sodium chlorite; a lower member having a predetermined configuration, said lower member being rigid and not reconfigurable thereby maintaining the configuration of dry acid disposed into a lower chamber, resulting in a continuously full lower chamber of said dry acid, said maintained configurations of said sodium chlorite and said acid cooperating to provide consistent chlorine dioxide generation irrespective of packet orientation; a dissolvable member disposed between and ultimately enclosed by said upper and lower members such that said upper and lower chambers have substantially equal volumes, whereupon, said upper and lower members are joined, thereby sealing said upper and lower chambers and enabling said joined upper and lower members to be disposed in water such that said lower member engages the water first, said joined upper and lower members ultimately swelling with absorbed water until all water has been absorbed; and a holder member for receiving a predetermined quantity of water and said joined upper and lower members with said dissolvable member therebetween, whereby said lower and upper member configurations cooperate to allow water to engage said dry acid mixture in the lower chamber followed by the now acidic liquid catalyst in the lower member being absorbed by the upper member through periphery contact at the sewn edges and engaging the substantially dry reactant in the upper chamber beginning the conversion of sodium chlorite to chlorine dioxide and to ultimately form slurries that completely dissolve the dissolvable member, thereby allowing said slurries to engage in the continuous reaction of chlorine dioxide by said acid slurry and sodium chlorite slurry to continuously produce chlorine dioxide gas until all chemicals have been exhausted, said chlorine dioxide gas passing through said upper and lower members and into a space to be disinfected and/or deodorized, said upper and lower members being dimensioned and configured to cooperate with selected quantities of dry sodium chlorite and dry acid mixtures to generate a predetermined quantity of chlorine dioxide gas over a predetermined time period, said predetermined quantity of water being absorbed relatively quickly by said lower member, then absorbed by said upper member through sewn edges after said joined lower and upper members are disposed in said water.

The invention further provides facilitating a chemical reaction comprising an upper member having a predetermined configuration; a lower member having a predetermined configuration; a dissolvable member disposed between and ultimately enclosed by said upper and lower members such that upper and lower chambers are formed having substantially equal volumes, said upper chamber ultimately receiving a dry sodium chlorite mixture and said lower chamber ultimately receiving a dry acid mixture, whereupon, said upper and lower members are joined, thereby sealing said upper and lower chambers and enabling said joined upper and lower members to be disposed in water such that said lower member engages the water first, said joined lower and upper members ultimately swelling with absorbed water until all water has been absorbed; and a holder member for receiving a predetermined quantity of water and said joined upper and lower members with said dissolvable member therebetween, whereby said upper and lower member configurations cooperate to allow a predetermined quantity of water to engage said dry acid and sodium chlorite mixtures to ultimately form slurries to dissolve said dissolvable member to allow said slurries to engage and ultimately react to generate chlorine dioxide gas that ultimately passes through said upper and lower members and into a space to be disinfected and/or deodorized, said upper and lower members being dimensioned and configured to cooperate with selected quantities of dry sodium chlorite and dry acid mixtures to generate a predetermined quantity of chlorine dioxide gas over a predetermined time period, said predetermined quantity of water being absorbed relatively quickly by said lower member, then absorbed by said upper member after said joined lower and upper members are disposed in said water.

The invention also provides a method for facilitating a chemical reaction, said method comprising the steps of: providing compressed cellulose sponge for the upper and lower members having dimensions in inches substantially about $2\frac{5}{8} \times 3\frac{3}{4} \times \frac{5}{16}$; providing compressed cellulose cloth having dimensions in inches of substantially about $2\frac{5}{8} \times 3\frac{3}{4} \times \frac{5}{16}$; providing soluble polyvinyl alcohol material for the dissolvable member having dimensions in inches relatively smaller than substantially about $2\frac{5}{8} \times 3\frac{3}{4} \times \frac{1}{32}$ to allow said polyvinyl alcohol material to be ultimately encased by said compressed cellulose sponge and said compressed cellulose cloth; disposing said polyvinyl alcohol material upon said compressed cellulose cloth; disposing said compressed cellulose sponge upon said polyvinyl alcohol material; securing together engaging peripheral portions of said compressed cellulose sponge, said compressed cellulose cloth and said soluble polyvinyl alcohol such that a side portion remains open; placing 16.5 grams of citric acid in a room having a humidity level at or less than twenty percent; disposing half of said acid mixture between said compressed cellulose cloth and said polyvinyl alcohol material; disposing a second dry reactant of five grams of sodium chlorite between said compressed cellulose sponge and said polyvinyl alcohol material; disposing the remaining half of said first acid mixture between said compressed cellulose cloth and said polyvinyl alcohol material; sealing said open side portion such that said first and second mixtures are isolated and sealed between respective walls formed from said compressed cellulose sponge, said compressed cellulose cloth and said polyvinyl alcohol, thereby forming a chlorine dioxide generating device; activating said chlorine dioxide generating device via sixty milliliters of relatively warm water disposed in a container, said chlorine dioxide generating device being disposed in said container such that said compressed cellulose cloth forms a lower portion of the device that engages the water before said compressed cellulose sponge engages the water, thereby causing chlorine dioxide gas to be emitted from said device until all reactions have exhausted and said water has been completely absorbed by said compressed cellulose sponge.

BRIEF DESCRIPTION OF THE DRAWINGS

These and other objects, advantages and novel features of the present invention, as well as details of an illustrative embodiment thereof, will be more fully understood from the following detailed description and attached drawings, wherein.

DESCRIPTION OF THE PREFERRED EMBODIMENT

Figure 1:
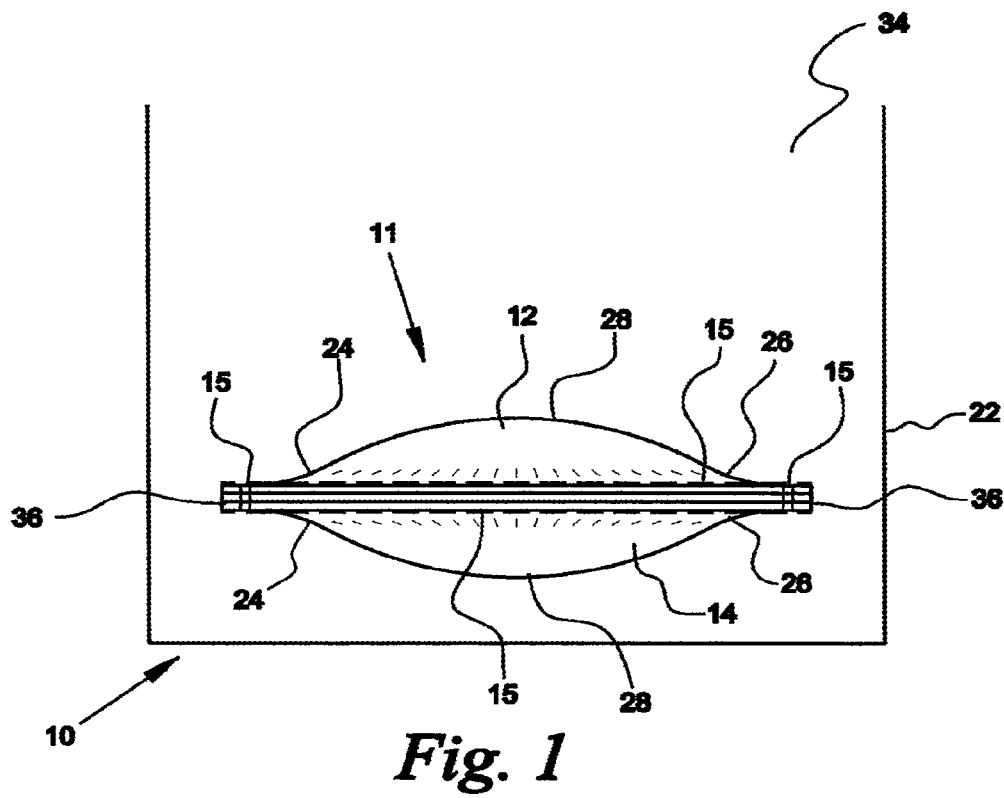
FIG. 1 is a front elevation view of a device for facilitating a chemical reaction in accordance with the present invention. The device includes a single packet in a holder.
Figure 2:
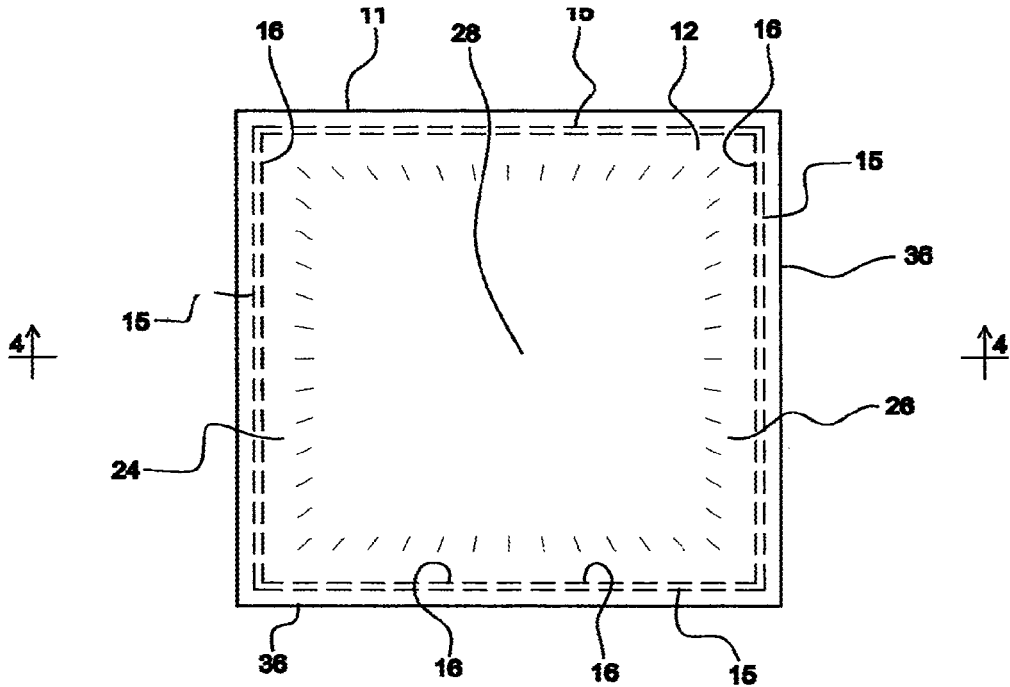
FIG. 2 is a top view of the single packet of FIG. 1.
Figure 3:
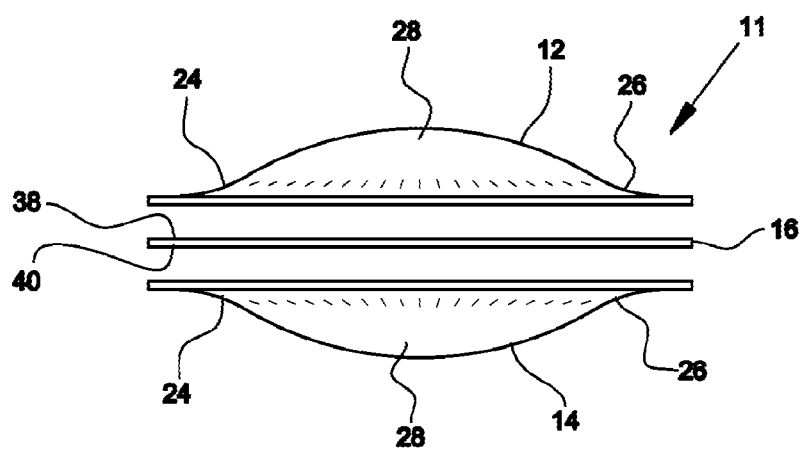
FIG. 3 is a front exploded view of the single packet of FIG. 2.

Referring now to FIGS. 1-5, a device fabricated from compressed cellulose for facilitating a chemical reaction between a liquid catalyst and one or more dry reactants within the device to produce a gas or liquid that is ultimately released into air or liquid is denoted as numeral 10. One use for the device 10 of the present invention is the generation of a gas by acid activation. Examples of acid activation include, but are not limited to acid activation of a carbonate via calcium carbonate combined with citric acid in the presence of moisture to form carbon dioxide, acid activation of a sulfite via sodium bisulfite or potassium bisulfite with fumaric acid and/or potassium bitartrate in the presence of moisture to form sulfur dioxide gas, and acid activation of a nitrite via sodium nitrite or potassium nitrite in the presence of moisture to form nitrogen dioxide gas.

A preferred use of the device 10 is the generation of chlorine dioxide gas for release into air or water. The device 10 includes a single packet 11 fabricated from a compressed cellulose material. The compressed cellulose material causes the packet 11 to be rigid thereby preventing the packet from deforming or otherwise changing configuration after disposing dry reactants into chambers, resulting in continuously full chambers of dry chemicals that maintain a constant configuration within the packet 11, which causes consistent chorine dioxide generation irrespective of packet 11 orientation. The single packet 11 includes an upper member 12 having a predetermined configuration, a lower member 14 having a predetermined configuration, a dissolvable member 16 disposed between and ultimately enclosed by the upper and lower members 12 and 14 such that upper and lower chambers 18 and 20 are formed having substantially equal volumes. The upper chamber 18 is substantially filled with sodium chlorite 30 and the lower chamber 20 is substantially filled with an acid mixture 32. The device 10 further includes a holder member 22 for receiving a predetermined quantity of liquid catalyst such as water, and for receiving the joined upper and lower members 12 and 14 with the dissolvable member 16, sodium chlorite 30 and acid mixture 32 therein.

Figure 4:
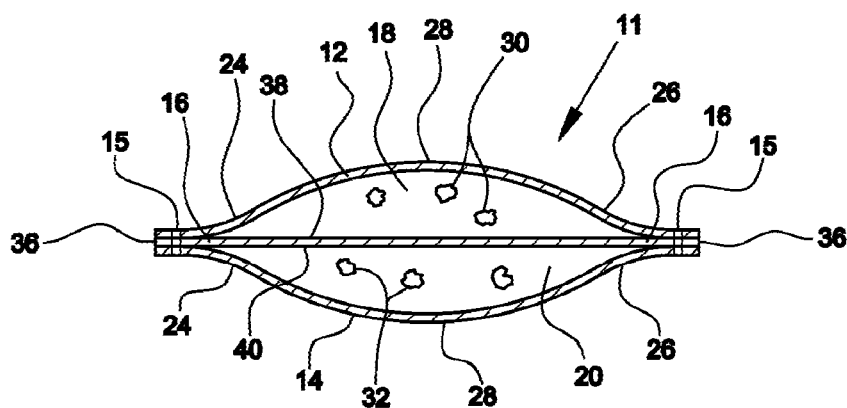
FIG. 4 is a sectional view taken along line 4-4 of FIG. 2.
Figure 5:
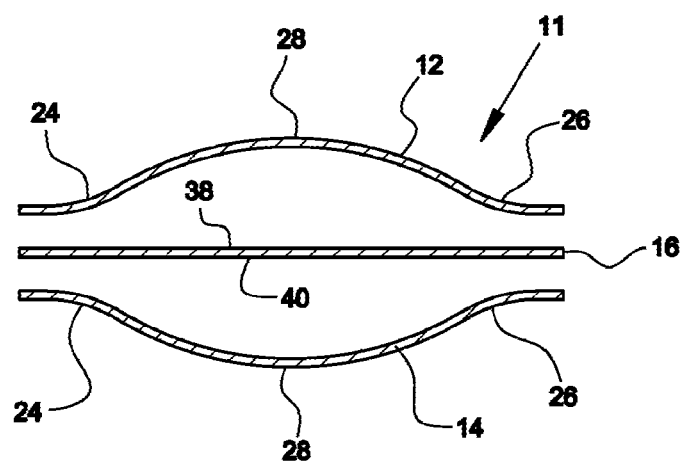
FIG. 5 is a front sectional view of the single packet of FIG. 3.
Figure 6:
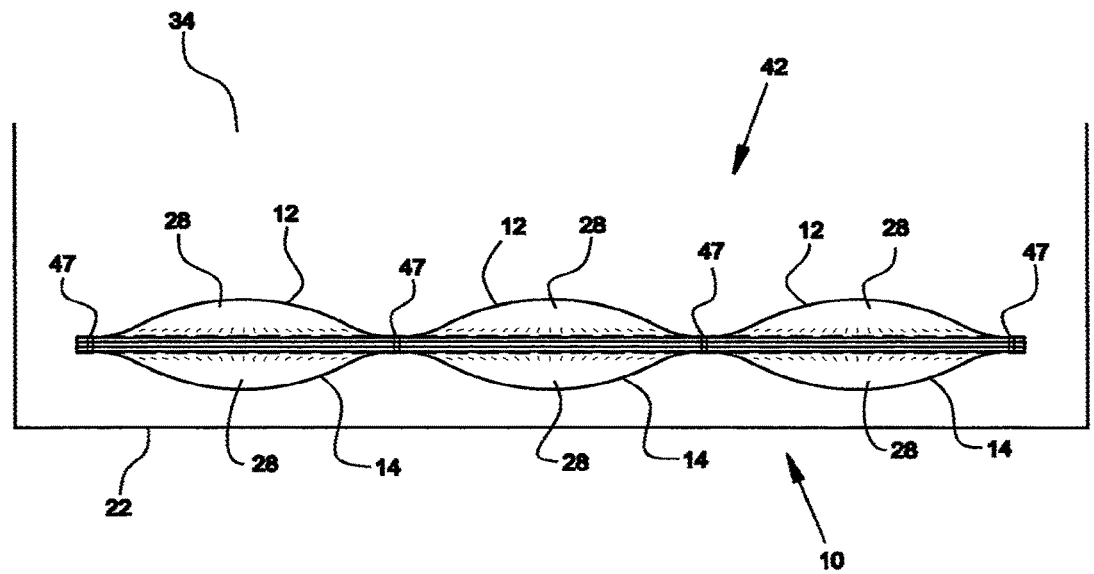
FIG. 6 is a front elevation view of an alternative device for facilitating a chemical reaction in accordance with the present invention. The device includes three packets.
Figure 7:
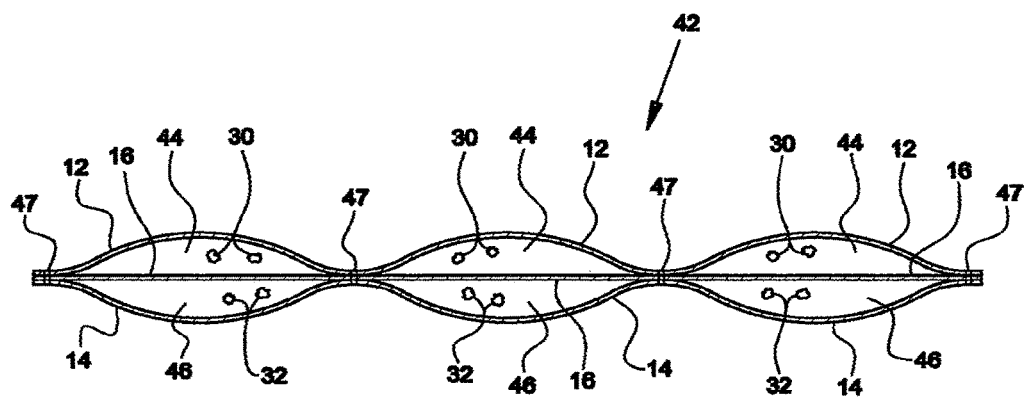
FIG. 7 is a sectional view taken along line 7-7 of FIG. 6.
Figure 8:
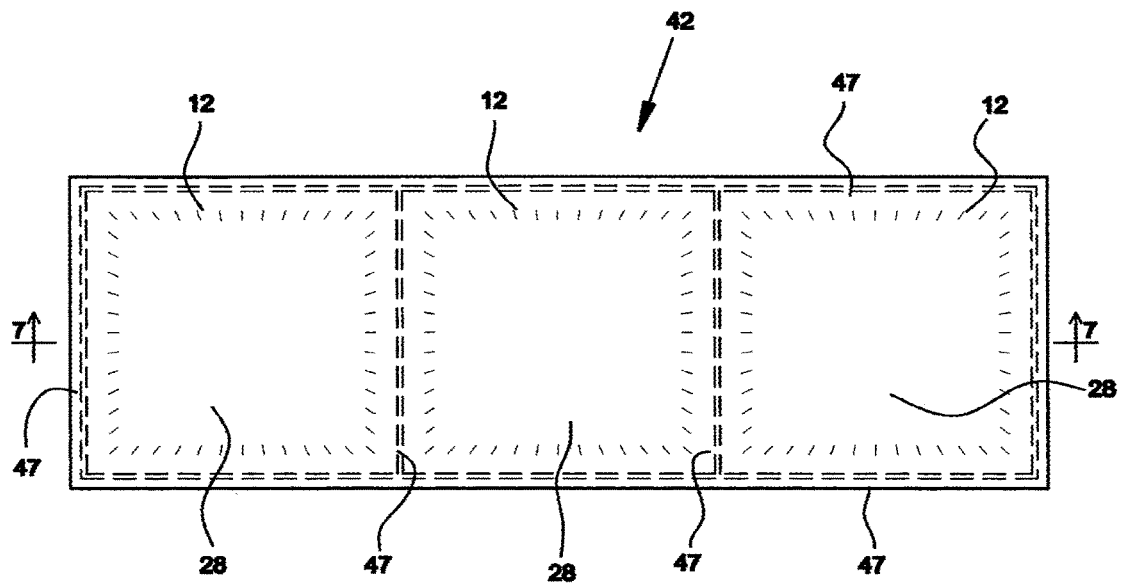
FIG. 8 is a top view of the three packets of FIG. 6.
Figure 9:
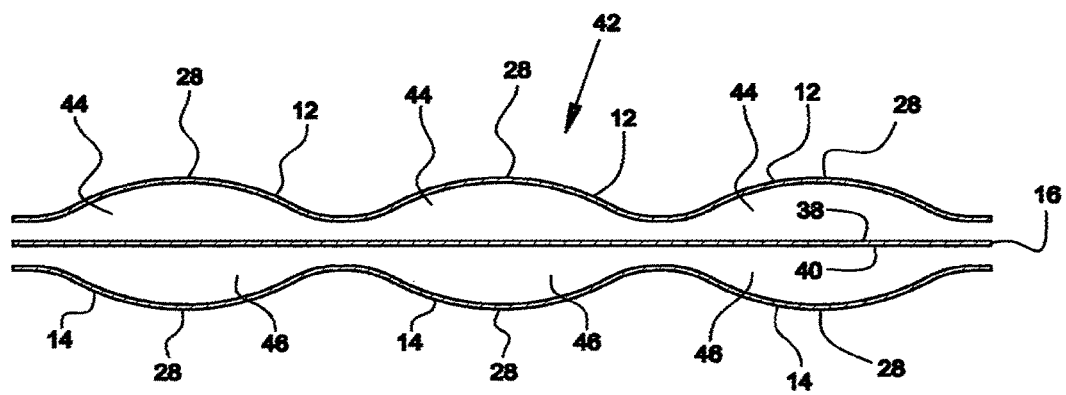
FIG. 9 is an exploded sectional view of the three packets of FIG. 7.

Referring to FIG. 4, the upper and lower members 12 and 14 include configurations having first and second arcuate end portions 24 and 26 with substantially planar central portions 28 therebetween. The arcuate end portions 24 and 26 cooperate with the central portions 28 to configure the upper and lower chambers 18 and 20 such that relatively large central portion volumes and relatively small edge portion volumes are formed in each chamber 18 and 20. The upper chamber 18 is substantially filled with a dry anhydrous sodium chlorite. The lower chamber 20 is substantially filled with a dry anhydrous acid 32, preferably citric acid; whereupon, the upper and lower members 12 and 14 are joined via stitching 15 (preferably a double stitch) or similar securing means, thereby sealing the upper and lower chambers 18 an 20 and enabling the joined upper and lower members 12 and 14 to be disposed in a predetermined volume of water in the holder member 22 such that the lower member 14 engages the water first. The lower member 14 quickly absorbs a volume of water substantially greater than the upper member 12. The upper and lower members 12 and 14 are sized and configured to cooperate and swell to absorb all the predetermined volume of water disposed in the holder member 22.

Referring to FIG. 1, the configuration of the holder member 22, when taking a top view of the member 22, corresponds to the configurations of the joined upper and lower members 12 and 14 such that a relatively rectangular configuration is presented by both the joined members 12 and 14, and the holder member 22. The configurations of the upper and lower members 12 and 14 promote a rate of absorbing water via the lower member 14 and the acid mixture 32 that ultimately results in an acid slurry in the lower chamber 20; and a rate of absorbing water via a periphery 36 of the upper member 12 joined to the periphery of the lower member 14, then into the sodium chlorite mixture to ultimately form a slurry in the upper chamber 18. The sodium chlorite slurry forms in the upper chamber 18 at a slower rate than the formation of the acid slurry in the lower chamber 20. Both slurries ultimately cooperate to dissolve the dissolvable member 16. The holder member 22 includes a recess 34 having a substantially rectangular configuration. The recess 34 has longitudinal and lateral dimensions slightly larger than corresponding longitudinal and lateral dimensions forming an outer perimeter or periphery 36 of the joined upper and lower members 12 and 14.

The holder member 22 receives a predetermined quantity of water and said joined upper and lower members 12 and 14 with said dissolvable member 16 therebetween. Said lower and upper member 14 and 12 configurations cooperate to allow water to engage the dry acid mixture 32 in the lower chamber 20 followed by the now acidic liquid catalyst in the lower member 14 being absorbed by the upper member 12 through periphery contact at the sewn edges 36 and engaging the substantially dry sodium chlorite 30 in the upper chamber 18, thereby beginning the conversion of sodium chlorite 30 to chlorine dioxide and to ultimately form slurries that completely dissolve the dissolvable member 16, thereby allowing said slurries to engage in the continuous reaction of the acid slurry and sodium chlorite slurry to continuously produce chlorine dioxide gas until all chemicals have been exhausted. The chlorine dioxide gas passes through the upper and lower members 12 and 14 and into a space to be disinfected and/or deodorized. The upper and lower members 12 and 14 are dimensioned and configured to cooperate with selected quantities of dry sodium chlorite 30 and dry acid 32 mixtures to generate a predetermined quantity of chlorine dioxide gas over a predetermined time period. The predetermined quantity of water is absorbed relatively quickly by the lower member 14, then absorbed by the upper member 12 through the sewn edges 36 after the joined lower and upper members 14 and 12 are disposed in the water.

The dissolving member 16 allows the slurries to engage and generate chlorine dioxide gas that passes mainly through the upper member 12 with a relatively small amount of chlorine dioxide gas passing through the lower member 14. The chlorine dioxide gas exits the joined upper and lower members 12 and 14, then naturally flows into a space to be disinfected and/or deodorized. The upper and lower members are dimensioned and configured to cooperate with selected quantities of dry sodium chlorite and dry acid mixtures to generate a predetermined quantity of chlorine dioxide gas over a predetermined time period. The predetermined quantity of water is absorbed relatively quickly by the lower and upper members 14 and 12 upon being disposed in a holder member recess 34 having dimensions slightly larger than corresponding dimensions of the periphery 36 of the joined upper and lower members 12 and 14. The configuration of the upper and lower members 12 and 14, allow a bottom compressed sponge cloth to engage the water and expand and be reconfigured such that the edges are contorted upward creating a cupping action or concave up configuration, resulting in a substantially wet acid engaging one side of the dissolvable member 16 and a substantially dry sodium chlorite engaging the opposite side of the dissolvable member 16. The now expanded bottom sponge cloth cooperates with the upper compressed sponge such that when the upper compressed sponge absorbs sufficient now acidified water to fully expand, the bottom sponge cloth reverts to a planar configuration to dispose the reactants of the upper and lower chambers 18 and 20 closer together. The upper and lower members 12 and 14 cooperate to allow a predetermined quantity of liquid catalyst to penetrate the lower member 14 and engage the dry acid reactant in the lower chamber 20.

The packet 11 is ultimately disposed in the liquid catalyst such that the lower member 14 or bottom compressed sponge cloth engages the liquid catalyst or water first, and expand and be reconfigured such that the edges 36 are contorted upward creating a cupping action or concave up configuration, resulting in a substantially wet acid 32 engaging one side of the dissolvable member 16 and a substantially dry sodium chlorite 30 engaging the opposite side of the dissolvable member 16. The now expanded bottom cellular cloth 14 (or sponge cloth) cooperates with the upper compressed sponge 12 such that when the upper compressed sponge 12 absorbs sufficient now acidified water to fully expand, the bottom sponge cloth 14 reverts to a planar configuration to dispose the reactants 30 and 32 of the upper and lower chambers 18 and 20 closer together. The lower and upper members 14 and 12 cooperate to allow a predetermined quantity of liquid catalyst to penetrate the lower member 14 and engage the acid reactant 32 in the lower chamber 20 followed by the now acidic liquid catalyst in the lower chamber 20 being absorbed by the upper member 12 through periphery contact at the sewn edges 47, the acidic liquid catalyst then engaging the substantially dry reactant 30 in the upper chamber 18, thereby beginning the conversion of sodium chlorite 30 to chlorine dioxide and ultimately forming slurries that completely dissolve the dissolvable member 16 to allow the slurries to engage in the continuous reaction of the chlorine dioxide until all chemicals have been exhausted.

The dissolvable member 16 has longitudinal and lateral dimensions relatively smaller than corresponding longitudinal and lateral dimensions of the upper and lower members 12 and 14, thereby allowing the dissolvable member 16 to be totally encased between the upper and lower members 12 and 14 after the members 12 and 14 are joined via water resistant thread sewn about the periphery 36 of cooperating edge portions of the upper and lower members 12 and 14, or similar joining means well known to those of ordinary skill in the art. A myriad of materials may be used to fabricate the dissolvable member 16 including, but not limited to starch, gelatin and the preferred material of fabrication-polyvinyl alcohol and starch provided by BioStartch Inc that are capable of withstanding the dry chemical mixtures until activation by the liquid catalyst. A non-absorbent fiberglass cloth, mesh or weave, or similar non-absorbent, non-soluble weave may be included in the dissolvable member 16 to strengthen the dissolvable member 16 material and/or to slow down or otherwise control the rate of reaction between upper and lower chambers 18 and 20, thereby controlling the amount of water that mixes with the sodium chlorite 30 and the acid mixture 32.

The upper member 12 is fabricated from a biodegradable, compressed cellulose sponge material having multiple pores that are closed when dry and open when wet. The upper member 12 material is manufactured by 3M Company and Spontex Company, both well known to those of ordinary skill in the art. The lower member 14 is fabricated from a biodegradable, compressed cellulose cloth material having multiple pores substantially smaller in size than the pores of the cellulose sponge material of the upper member 12 pores. The lower member 14 material is manufactured from 3M and Spontex Companies. The upper and lower member 12 and 14 pores are closed when dry and open when wet. The closed pores of the upper and lower members 12 and 14 prevent the sodium chlorite and acid mixture 30 and 32 from combining with moisture to start a premature reaction and/or from escaping the packet before activation. When the closed pores of the upper and lower members 12 and 14 open, the generation of chlorine dioxide gas is initiated and allowed to escape to through the upper and lower members 12, thereby preventing a pressure buildup of the generated gas, which can result in the spontaneous combustion or explosion of the chlorine dioxide gas.

The higher density of pores of the lower member 14 allow the lower member 14 to absorb and hold more water than the pores of the upper member 12. The upper member 12 pores become relatively larger than the lower member 14 pores when wet, thereby allowing a relatively large quantity of chlorine dioxide gas to escape from the upper member 12 in comparison to the lower member 14. The primary purpose for the pores of the upper member 12 is for gas release, and a secondary purpose for the pores being the absorbing of water. The primary purpose for the pores of the lower member 14 is for water absorbing, and a secondary purpose for the pores being gas release. The lower member 14 not only absorbs water via the pores, but also via the fiber material that forms the lower member 14. The sponge material of the upper member 12 has less fiber than the lower member 14 and correspondingly absorbs less water. Besides the smaller pores of the lower member 14 impeding chlorine dioxide gas flow, engagement between the lower member 14 and the holding member 22 also restricts chlorine dioxide gas flow. The upper and lower members 12 and 14 hold the absorbed water during the entire reaction time for forming chlorine dioxide gas. The surface areas for the upper and lower members 12 and 14 are relatively small before submersion and relatively large when exposed to water during the entire reaction time for forming chlorine dioxide gas.

Referring to FIGS. 6-9, a multi-chamber packet 42, which is used for releasing chlorine dioxide gas into air, is depicted with three upper chambers 44 and three lower chambers 46. Each chamber 44 and 46 is substantially the same configuration and dimensions as the corresponding chambers 18 and 20 of the single packet 11 of FIGS. 1-5. Each chamber 44 and 46 has a peripheral stitching 47 (preferably a double stitch) that captures the sodium chlorite or acid mixtures in respective sealed and separated chambers 44 and 46.

The multi-chamber packet 42 provides for more generation of chlorine dioxide gas from the multi-chamber packet 42 compared to the single packet 11, when each individual chamber of the multi-chamber packet 42 is substantially equal in volume to the single packet 11. Obviously, a relatively larger single packet 11 could be used to generate more chlorine dioxide gas; however, a larger single packet 11 is not efficient due to the corresponding larger quantity of sodium chlorite 30 in the upper chamber 18 ultimately combining with water to form a "caked" or hardened central core surrounded by relatively wet powder. The hardened core of sodium chlorite 30 prevents the acid mixture 32 from fully dissolving and activating the sodium chlorite 30 after the acid mixture 32 dissolves the dissolvable member 16 and engages the sodium chlorite 30, resulting in wasted quantities of both the sodium chlorite 30 and the acid mixture 32. The separated chambers 44 and 46 of the multi-chamber packet 42 provide smaller chamber quantities of the sodium chlorite 30 and acid mixture 32 for promoting faster and more complete reactions, thereby generating more chlorine dioxide gas from the pre-selected quantity of all sodium chlorite 30 and acid mixture 32 in all the chambers 44 and 46 of the multi-chamber packet 42, than the amount of chlorine dioxide gas generated from the same pre-selected quantity of sodium chlorite 30 and acid mixture 32 disposed in larger single chambers 18 and 20 in a correspondingly larger single packet 11.

The single packet 11 of FIGS. 1-5 and the multi-chamber packet 42 of FIGS. 6-9, may be used to release chlorine dioxide gas into water by using a higher density cellulose material with greater numbers and greater density of smaller pores for the upper members 12 forming the upper chambers 18 and 44. The compressed cellulose material for the upper member 12 is substantially the same as the cellulose material (manufactured from 3M and Spontex Companies) used for the lower members 14 forming the lower chambers 20 and 46. The higher pore density of the compressed cellulose cloth of the upper and lower members 12 and 14 allows water to pass therethrough to form a sodium chlorite slurry in the upper chambers 18 and 44 and an acid slurry in the lower chamber 20 and 46, whereupon, the slurries dissolve the dissolvable members 16 and ultimately mix and react to release chlorine dioxide gas through the pores of the cellulose material before the slurries diffuse or otherwise "escape" from the upper chambers 18 and 44 and the lower chambers 20 and 46, and into the surrounding liquid mass or water.

The compressed cellulose cloth of the upper and lower members 12 and 14 includes an outer surface or "skin" for retaining water in the pores of the cloth. The skin replaces the open pores on the surface of the cloth. More specifically, there are no open pores on the surface of the cloth, but there are ultimately small open pores inside the cell structure of the inner layers of the cloth material, thereby allowing generated chlorine dioxide gas to escape from the packets 11 and 42 via the open pores and through spaces between the fibers of the caused by water contacting the cloth material. Both the single packet 11 and the multi-chamber packet 42 require a weight secured thereto to maintain the respective packet under water in a vertical or horizontal orientation. Attaching the weight to the respective packet is well known to those of ordinary skill in the art.

Figure 10:
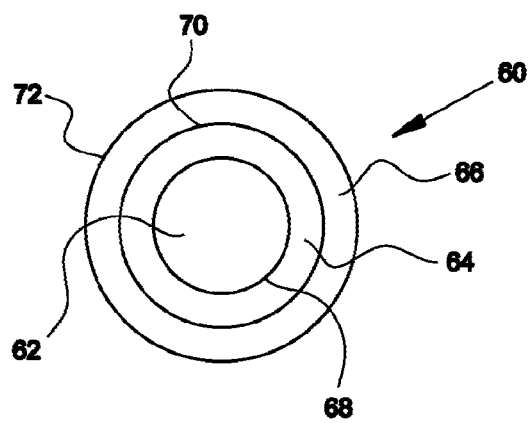
FIG. 10 is an internal view of a nested chamber packet in accordance with the present invention.

Referring to FIG. 10, a nested chamber packet 60 is depicted for use when chlorine dioxide is released in water. The nested chamber packet 60 must be maintained under water via a weight or similar means as detailed above for the multi-chamber packet 42. FIG. 10 includes three nested chambers, an inner chamber 62, a middle chamber 64 and an outer chamber 66. The inner chamber 62 includes sodium chlorite 30 surrounded by a compressed cellulose sponge 68. The middle chamber 64 includes sodium chlorite 30 surrounded by a compressed cellulose sponge 70. The outer chamber 66 includes an acid mixture 32 surrounded by a compressed cellulose cloth 72. The cellulose cloth 72 slowly allows water to enter the outer chamber 66 and form an acid slurry that ultimately penetrates the sponge 70 of the middle chamber 64 followed by the acid slurry penetrating the sponge 68 of the inner chamber, thereby extending the release time for the chlorine dioxide gas from the nested chamber packet 60 to sanitize or disinfect a water volume, pools and cooling towers for example, for a time period much longer than the aforementioned single and multi-chamber packets 11 and 42.

Figure 11:
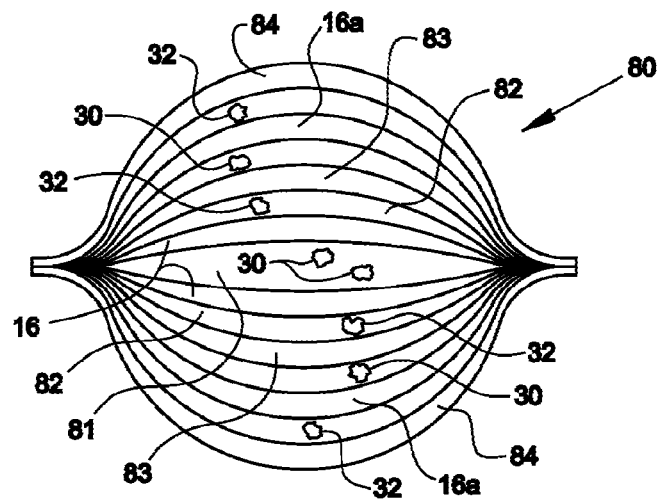
FIG. 11 is an internal view of a multilayer packet in accordance with the present invention.

Referring to FIG. 11, a multi-layer "onion" packet 80 is depicted for increasing the release time for chlorine dioxide into water. The multi-layer packet 80 is maintained under water via a weight or similar means as detailed above. The center core chamber 81 contains sodium chlorite 30 and is defined by two dissolvable members 16. The next layer 82 is an acid mixture 32 captured between the two dissolvable members 16 and two compressed cellulose sponge members 83. The next layer is sodium chlorite 30 captured between the two cellulose sponge member 83 and two dissolvable members 16*a*. The next layer is an acid mixture 32 captured between the two dissolvable members 16*a* and two cooperating compressed cellulose cloth members 84 that form an outer shell.

Irrespective of the type of packet used, all packets should be placed in a moisture resistant package to prevent the premature combination and reaction of the sodium chlorite and acid mixtures. For safety, the holder member should include a cover to prevent water containing chlorine dioxide gas from escaping and/or improperly disposed, and for maintaining chlorine dioxide as inside the holder member 22.

The aforementioned packets can have a myriad of sizes and configuration for a predetermined volume of air or water to be disinfected and deodorized. However, the chamber sizes and the corresponding ratios for the respective chemical mixtures within the chambers will remain substantially constant. For example, an upper chamber 18 sized to contain a dry sodium chlorite mixture of five grams will be joined to a lower chamber 20 having a dry acid mixture quantity of substantially about 16.5 grams of citric acid anhydrous. The quantity of water disposed in the holder member 22 to react with the above quantities is substantially about sixty milliliters. The dimensions of the compressed cellulose sponge forming the upper member 12 is substantially about $2\frac{5}{8} \times 3\frac{3}{4} \times \frac{5}{16}$ inches. The dimensions of the compressed cellulose cloth forming the lower member 14 is substantially about $2\frac{5}{8} \times 3\frac{3}{4} \times \frac{5}{16}$ inches. The dimensions of the dissolvable member 16 is relatively smaller than substantially about $2\frac{5}{8} \times 3\frac{3}{4} \times \frac{1}{32}$ inches.

The method for fabricating the single packet 11 includes the following steps:

disposing said polyvinyl alcohol material upon said compressed cellulose cloth;

disposing said compressed cellulose sponge upon said polyvinyl alcohol material;

securing together engaging peripheral portions of said compressed cellulose sponge, said compressed cellulose cloth and said polyvinyl alcohol such that a side portion remains open;

providing substantially about sixteen and one-half grams of citric acid in a room having a humidity level at or less than twenty percent;

disposing half of said first mixture between said compressed cellulose cloth and said polyvinyl alcohol material;

disposing a second mixture consisting of five grams of sodium chlorite between said compressed cellulose sponge and said polyvinyl alcohol material;

disposing the remaining half of said first mixture between said compressed cellulose cloth and said polyvinyl alcohol material;

sealing said open side portion such that said first and second mixtures are isolated and sealed between respective walls formed from said compressed cellulose sponge, said compressed cellulose cloth and said polyvinyl alcohol, thereby forming a chlorine dioxide generating device;

activating said chlorine dioxide generating device via sixty milliliters of relatively warm water disposed in a container, said chlorine dioxide generating device being disposed in said container such that said compressed cellulose cloth forms a lower portion of the device that engages the water before said compressed cellulose sponge engages the water, thereby causing chlorine dioxide gas to be emitted from said device until all reactions have exhausted and said water has been completely absorbed by said compressed cellulose.

Figure 12:
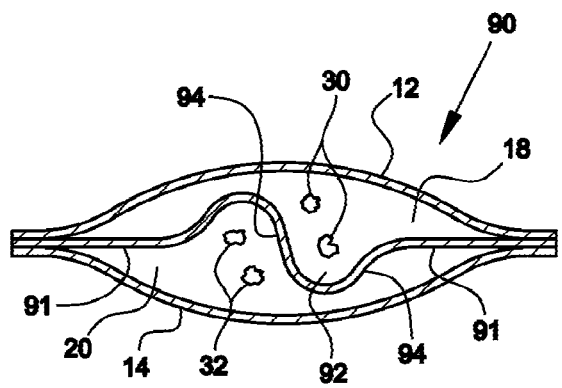
FIG. 12 is the single packet sectional view of FIG. 4 but with an alternative configuration for the dissolvable member in accordance with the present invention.

Referring now to FIG. 12, a sectional side view of a single packet 11 depicts an alternative configuration for the dissolvable member 16 of FIG. 4, the alternative configuration being denoted as numeral 90. The dissolvable member 91 can be used with the single packet 11 or the multi-chamber packet 42 for generating chlorine dioxide gas into air or water. The dissolvable member 91 includes an undulating or "wave" configuration that is formed via the above detailed steps for fabricating the single packet 11. The dissolvable member 91 provides a trough or recess 92 that receives sodium chlorite 30 therein. The upper and lower chambers 18 and 20 are completely filled with sodium chlorite 30 and acid mixture 32, thereby forcibly maintaining sodium chlorite 30 in the recess 92 irrespective of the orientation of the packet 11 and 42. The conical wall 94 of the recess 92 of the dissolvable member 91 provides more surface area than a planar dissolvable member 16, thereby increasing cooperating quantities of sodium chlorite 30 and acid mixture 32 disposed adjacently on opposite sides of the dissolvable member 91. When the dissolvable member 91 is dissolved by acid and sodium chlorite slurries, the increased quantities of sodium chlorite and acid slurries that immediately mix together ultimately generates chlorine dioxide gas at a faster rate than the gas rate generated by relatively smaller slurry quantities that mix after a planar dissolvable member 16 is dissolved. Thus, the gas generation rate for the packets 11 and 42 can be increased or decreased by correspondingly increasing or decreasing the surface area of the recess 92, and the surface area of the recess 92 is varied by correspondingly changing the configuration and/or dimensions of the dissolvable member 91.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims. It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled.

The invention claimed is:

1. A device for facilitating a chemical reaction comprising:
    a first packet member defining a first chamber portion, said first packet member being formed of a water permeable, first compressed cellulose material having a first average pore diameter;
    a second packet member defining a second chamber portion, said second packet member being formed of a water permeable, second compressed cellulose material having a second average pore diameter that is greater than said first average pore diameter;
    a first dry ingredient disposed in said first chamber portion; and
    a second dry ingredient disposed in said second chamber portion;
    said first packet member being attached to said second packet member; and
    wherein said first dry ingredient and said second dry ingredient are configured to form chlorine dioxide in the presence of water.

2. A kit for using the device of claim 1, including a container for receiving the device of claim 1, said container being sized to receive a pre-determined amount of a liquid catalyst for facilitating a reaction between said first dry ingredient and said second dry ingredient within said packet.

3. The device of claim 1, wherein said first chamber portion and said second chamber portion are dimensioned so as to accommodate a substantially equal amount of said first dry ingredient and said second dry ingredient.

4. The device of claim 1, wherein said first chamber portion and said second chamber portion are dimensioned so as to accommodate a substantially equal amount of said first dry ingredient and said second dry ingredient.

5. The device of claim 1, wherein said first dry ingredient comprises dry sodium chlorite.

6. The device of claim 5, wherein said second dry ingredient comprises at least one dry acid selected from the group consisting of citric acid, boric acid, lactic acid, tartaric acid, maleic acid, malic acid, glutaric acid, adipic acid, acetic acid, formic acid, sulfamic acid, sulfuric acid, hydrochloric acid, phosphoric acid, phosphoric anhydride, sulfuric anhydride, maleic anhydride, calcium chloride, magnesium chloride, magnesium nitrate, lithium chloride, magnesium sulfate, aluminum sulfate, sodium acid sulfate, sodium dihydrogen phosphate, potassium acid sulfate, potassium dihydrogen phosphate, and sodium persulfate.

7. The device of claim 1, wherein each of the first packet member and the second packet member have dimensions substantially about 2⅝ inches×3¾ inches×5/16 inches.

8. A device for facilitating a chemical reaction comprising:
  a holder member for receiving a predetermined quantity of liquid catalyst;
  a packet comprising a first compressed cellulose member, defining a first chamber containing a pre-determined quantity of a first dry ingredient and a second compressed cellulose member defining a second chamber containing a pre-determined quantity of a second dry ingredient;
  said first compressed cellulose member having an average pore size that is less than the average pore size of said second compressed cellulose member; and
  said packet being disposed within said holder and said liquid catalyst such that at least said first compressed cellulose member is at least partially disposed within said liquid catalyst;
  wherein said first dry ingredient and said second dry ingredient are configured to form chlorine dioxide in the presence of water.

9. The device of claim 8, wherein said first dry ingredient comprises dry sodium chlorite and said second dry ingredient comprises at least one dry acid selected from the group consisting of citric acid, boric acid, lactic acid, tartaric acid, maleic acid, malic acid, glutaric acid, adipic acid, acetic acid, formic acid, sulfamic acid, sulfuric acid, hydrochloric acid, phosphoric acid, phosphoric anhydride, sulfuric anhydride, maleic anhydride, calcium chloride, magnesium chloride, magnesium nitrate, lithium chloride, magnesium sulfate, aluminum sulfate, sodium acid sulfate, sodium dihydrogen phosphate, potassium acid sulfate, potassium dihydrogen phosphate, and sodium persulfate.

10. A method of making a device for facilitating a chemical reaction comprising:
  preparing a first packet member, having a width, a length, and a first average pore size from a first water permeable, compressed cellulose material;
  preparing a second packet member from a second water permeable, compressed cellulose material, said second packet member having a width and length that is substantially the same as that of said first packet member and a second average pore size that is greater than said first average pore size;
  preparing a third packet member having a width and length that is substantially the same as that of said first packet member and said second packet member;
  placing said third packet member between said first packet member and said second packet member;
  partially joining said first packet member, and said second packet member, and said third packet member so as to form a packet such that at least one side of said packet remains substantially open, said first packet member defining a first chamber, and said second packet member defining a second chamber;
  substantially filling said first chamber with a first dry ingredient;
  substantially filling said second chamber with a second dry ingredient; and
  closing said at least one side of said packet.

11. The method of claim 10, wherein said first dry ingredient comprises dry sodium chlorite and said second dry ingredient comprises at least one dry acid selected from the group consisting of citric acid, boric acid, lactic acid, tartaric acid, maleic acid, malic acid, glutaric acid, adipic acid, acetic acid, formic acid, sulfamic acid, sulfuric acid, hydrochloric acid, phosphoric acid, phosphoric anhydride, sulfuric anhydride, maleic anhydride, calcium chloride, magnesium chloride, magnesium nitrate, lithium chloride, magnesium sulfate, aluminum sulfate, sodium acid sulfate, sodium dihydrogen phosphate, potassium acid sulfate, potassium dihydrogen phosphate, and sodium persulfate.

12. The method of claim 10, further comprising the step of forming a holder for accepting said device and a predetermined amount of liquid catalyst.

13. The method of claim 10, wherein each of the first packet member and the second packet member have dimensions substantially about 2⅝ inches×3¾ inches×5/16 inches.

* * * * *